United States Patent
Kato et al.

(10) Patent No.: US 9,523,568 B2
(45) Date of Patent: Dec. 20, 2016

(54) WAVELENGTH-SWEPT LIGHT SOURCE APPARATUS AND MEASURING APPARATUS

(71) Applicant: TOMEY CORPORATION, Nagoya-shi, Aichi (JP)

(72) Inventors: Chihiro Kato, Nagoya (JP); Yuji Nozawa, Nagoya (JP)

(73) Assignee: TOMEY CORPORATION, Nagoya-Shi (JP)

( * ) Notice: Subject to any disclaimer, the term of this patent is extended or adjusted under 35 U.S.C. 154(b) by 100 days.

(21) Appl. No.: 14/636,378

(22) Filed: Mar. 3, 2015

(65) Prior Publication Data

US 2015/0255951 A1 Sep. 10, 2015

(30) Foreign Application Priority Data

Mar. 4, 2014 (JP) .................................. 2014-041599

(51) Int. Cl.

| | | |
|---|---|---|
| *G01B 11/02* | (2006.01) | |
| *G01B 9/02* | (2006.01) | |
| *H01S 5/0683* | (2006.01) | |
| *H01S 5/068* | (2006.01) | |
| *A61B 3/10* | (2006.01) | |
| *H01S 5/14* | (2006.01) | |

(52) U.S. Cl.
CPC ....... *G01B 9/02004* (2013.01); *G01B 9/02091* (2013.01); *H01S 5/06821* (2013.01); *H01S 5/06837* (2013.01); *A61B 3/102* (2013.01); *H01S 5/143* (2013.01)

(58) Field of Classification Search
CPC ........ H01S 5/183; H01S 3/1305; H01S 5/141; A61B 3/00; G01B 9/02004; G01B 9/02091

See application file for complete search history.

(56) References Cited

U.S. PATENT DOCUMENTS 5,009,505 A * 4/1991 Malvern ................. G01K 11/32
250/227.19
5,600,442 A * 2/1997 Minegishi .............. G01D 5/266
356/498

(Continued)

FOREIGN PATENT DOCUMENTS

EP 2633803 9/2013
JP 2010-177328 8/2010

(Continued)

OTHER PUBLICATIONS

Extended European Search Report from European Appln. No. 15305324.4 dated Jun. 24, 2015.

*Primary Examiner* — Kara E Geisel
*Assistant Examiner* — Maurice Smith
(74) *Attorney, Agent, or Firm* — Grossman, Tucker, Perreault & Pfleger, PLLC

(57) ABSTRACT

A wavelength-swept light source apparatus comprises a light source that emits a wavelength-swept light that varies in a predetermined cycle, a mode hop detector that detects a mode hop of the wavelength-swept light emitted from the light source; and a control unit that controls at least one of a parameter that defines a specified period having a predetermined fixed or variable time length provided in the predetermined cycle and a control parameter of the light source, thereby to set an occurrence timing of the mode hop detected by the mode hop detector outside of the specified period.

11 Claims, 13 Drawing Sheets

(56) References Cited

U.S. PATENT DOCUMENTS

| | | | |
|---|---|---|---|
| 2008/0247429 A1 | 10/2008 | Colbourne | |
| 2013/0229627 A1 | 9/2013 | Kato et al. | |
| 2014/0028997 A1* | 1/2014 | Cable | G01B 9/02091 356/51 |
| 2015/0138530 A1 | 5/2015 | Luethi et al. | |

FOREIGN PATENT DOCUMENTS

| | | |
|---|---|---|
| JP | 5103412 | 12/2012 |
| WO | 2013/167525 | 11/2013 |

* cited by examiner

WAVELENGTH-SWEPT LIGHT SOURCE APPARATUS AND MEASURING APPARATUS

CROSS-REFERENCE TO RELATED APPLICATIONS

This application claims the benefit of Japanese Patent Application No. 2014-041599 filed Mar. 4, 2014 in the Japan Patent Office, and the entire disclosure of which is incorporated herein by reference.

BACKGROUND

The present invention relates to a wavelength-swept light source apparatus and a measuring apparatus.

Measuring apparatus, etc. that utilize wavelength characteristics of light have been developed in the fields of such as spectroscopy, surface profiling, and optical sensing. Various types of light sources have been proposed that emit light suitable for these applications. As one of such light sources, a wavelength-swept light source is known in which a wavelength of light emitted varies with time (for example, see Japanese Patent No. 5103412).

Various types of the wavelength-swept light sources are also known, such as, for example, a MEMS-type light source using a rotary mirror that rotates back and forth about its axis, a light source with a polygon mirror that rotates in one direction around its axis, and so on.

SUMMARY

All the types of the above-mentioned wavelength-swept light sources have a problem in which it is difficult to suppress occurrence of a mode hop in the middle of sweeping the wavelength. Mode hop means that the wavelength of the light emitted changes discontinuously. In a measuring apparatus that utilizes the above-mentioned wavelength characteristics of light, a mode hop in which the wavelength of light changes discontinuously, if occurs, leads to undesirable effects such as distortion and turbulence in measurement results obtained.

In the above-mentioned known Patent, for the purpose of providing a mode-hop-free light source, there is disclosed a method of finding and keeping a constant injection current that minimizes occurrence of a mode hop. Other known methods are a method of keeping the temperature of the light source constant, a method of providing a mode-hop-free light source by fine adjustment of arrangement of optical components comprised in the light source, etc. All these methods require a complex control, and thus have a problem in which it is difficult to provide a mode-hop-free light source.

The present invention has been made to solve the above problems, and an object thereof is to provide a wavelength-swept light source apparatus and a measuring apparatus that can suppress occurrence of problems caused by a mode hop, even if a light source in which a mode hop occurs is used.

To achieve the above object, the present invention provides the following means.

A wavelength-swept light source apparatus of the present invention comprises a light source, a mode hop detector, and a control unit. The light source emits a wavelength-swept light of which wavelength varies in a predetermined cycle. The mode hop detector detects a mode hop of the wavelength-swept light emitted from the light source. The control unit controls at least one of a parameter that defines a specified period having a predetermined fixed or variable time length provided in the predetermined cycle or a control parameter of the light source, thereby to set an occurrence timing of the mode hop detected by the mode hop detector outside of the specified period.

According to the wavelength-swept light source apparatus of the present invention, when a mode hop occurs in a wavelength-swept light emitted from the light source, the occurrence is detected by the mode hop detector. The control unit, when a mode hop occurs within the specified period, performs a control to change at least one of the occurrence timing of the mode hop and the specified period. Thereby, the mode hop occurs or exists outside of the specified period. In other words, occurrence or existence of the mode hop within the specified period is suppressed.

It is preferred that the light source in the invention described above comprises a light-emitting element that emits light, and the control unit controls an injection current supplied to the light-emitting element as the control parameter of the light source, thereby to set a timing of the mode hop detected by the mode hop detector outside of the specified period.

By controlling the injection current supplied to the light-emitting element, the occurrence timing of the mode hop in the wavelength-swept light emitted from the light source varies. Therefore, correlation between the specified period and the occurrence timing of the mode hop described above varies. Occurrence or existence of the mode hop within the specified period is suppressed. The control of the injection current, for example, can be a control of a value of the supplied current.

In the above invention, it is preferred that the light source comprises a light-emitting element that emits light and a temperature controller that adjusts a temperature of the light emitting element, wherein the control unit controls the temperature of the light emitting element by the temperature controller as the control parameter of the light source, thereby to set a timing of the mode hop detected by the mode hop detector outside of the specified period.

By controlling the temperature of the light-emitting element as such, the occurrence timing of the mode hop in the wavelength-swept light emitted from the light source varies. Therefore, correlation between the specified period and the occurrence timing of the mode hop described above varies. Occurrence or existence of the mode hop within the specified period is suppressed.

In the above invention, it is preferred that the light source comprises a light-emitting element that emits light and a wavelength sweep unit that sweeps the wavelength of the light emitted from the light-emitting element according to the predetermined cycle, wherein the control unit controls wavelength sweep characteristics in the wavelength sweep unit as the control parameter of the light source, thereby to set a timing of the mode hop detected by the mode hop detector outside of the specified period.

By controlling the wavelength sweep characteristics of the wavelength sweep unit in this manner, a width of wavelength variation in the wavelength-swept light emitted from the light source and a variation cycle vary. As a result of this change, the occurrence timing of the mode hop in the wavelength-swept light also varies. Therefore, correlation between the specified period and the occurrence timing of the mode hop described above varies. Occurrence or existence of the mode hop within the specified period is suppressed.

In the above invention, it is preferred that the control unit controls a relative position of the specified period to the predetermined cycle as a parameter that defines the specified period, thereby to set a timing of the mode hop detected by the mode hop detector outside of the specified period.

By thus controlling the relative position of the specified period, correlation between the specified period and the occurrence timing of the mode hop described above varies. Occurrence or existence of the mode hop within the specified period is suppressed.

In the above invention, it is preferred that the mode hop detector is a light intensity sensor that detects a light intensity of the wavelength-swept light emitted from the light source, and performs detection of the mode hop based on a change of the detected light intensity.

By detecting the light intensity of the emitted wavelength-swept light by the light intensity sensor this way, it is possible to indirectly detect the wavelength of the wavelength-swept light. In other words, since the wavelength and the light intensity in the wavelength-swept light are in one-to-one relation, the wavelength can be known by detecting the light intensity. Also, even occurrence of the mode hop outside of the specified period can be detected. Therefore, it is always possible to perform a control to change at least one of the occurrence timing of the mode hop and the specified period. In addition, if a light intensity sensor that measures light intensity of the wavelength-swept light exists for other purposes, the sensor can be shared.

In the above invention, it is preferred that the mode hop detector is a frequency detector that detects a frequency of the wavelength-swept light emitted from the light source, and performs detection of the mode hop based on a relation between the detected frequency and a light intensity corresponding to the frequency.

By thus using the frequency detector, it is possible to detect the frequency of the wavelength-swept light. Therefore, it is possible to directly detect the mode hop in the wavelength-swept light. Also, even occurrence of a mode hop outside of the specified period can be detected. Therefore, it is always possible to perform a control to change at least one of the occurrence timing of the mode hop and the specified period.

In the above invention, it is preferred that the wavelength-swept light source apparatus further comprises a light splitting element that splits the wavelength-swept light emitted from the light source into two, a first optical path that passes one of the split wavelength-swept light, a second optical path that passes the other of the split wavelength-swept light, a combining element that combines the one of the wavelength-swept light that has passed through the first optical path and the other of wavelength-swept light that has passed through the second optical path thereby to generate an interference light, and a light receiving element that detects an interference signal based on the interference light, wherein the mode hop detector detects the mode hop based on a time change of a signal strength in the interference signal.

As above, based on the time change of the signal strength in the interference signal, it is possible to detect that the mode hop has occurred within the specified period. That is, if the mode hop occurs within the specified period, a mode of the time change of the signal strength in the interference signal changes, as compared to a case where the mode hop does not occur in the specified period. Occurrence of the mode hop within the specified period can be detected by detecting this change.

In the above invention, it is preferred that the wavelength-swept light source apparatus further comprises a light splitting element that splits the wavelength-swept light emitted from the light source into two, a first optical path that passes one of the split wavelength-swept light, a second optical path that passes the other of the split wavelength-swept light, and a combining element that combines the one of the wavelength-swept light that has passed through the first optical path and the other of wavelength-swept light that has passed through the second optical path thereby to generate an interference light, and a light receiving element that detects an interference signal based on the interference light, wherein the mode hop detector detects the mode hop based on a shape of a peak in a relation between a frequency in the interference signal and a signal strength corresponding to the frequency.

As above, based on the shape of the peak in the relation between the frequency in the interference signal and the signal strength corresponding to the frequency, it is possible to detect that the mode hop has occurred within the specified period. That is, when the mode hop occurs in the wavelength-swept light, the shape of the peak changes, as compared to a case where the mode hop does not occur in the wavelength-swept light. Occurrence of the mode hop within the specified period can be detected by detecting this change.

A measuring apparatus of the present invention comprises the wavelength-swept light source apparatus of the present invention, a light splitting element that splits a wavelength-swept light emitted from the wavelength-swept light source apparatus into two, a first optical path that passes one of the split wavelength-swept light, a second optical path that passes the other of the split wavelength-swept light towards an object to be measured and the other of wavelength-swept light reflected from the object to be measured, a combining element that combines the one of the wavelength-swept light that has passed through the first optical path and the other of wavelength-swept light that has been reflected from the object to be measured and has passed through the second optical path thereby to generate an interference light, a light receiving element that outputs an interference signal based on the interference light, and an analysis unit that acquires the interference signal in the specified period and obtains a position of each part of the object to be measured based on a peak in a relation between a frequency of the acquired interference signal and a signal strength corresponding to the frequency.

The measuring apparatus of the present invention comprises the wavelength-swept light source apparatus of the present invention, and the analysis unit that acquires the interference signal in the specified period and obtains a position of each part of the object to be measured based on a peak in a relation between a frequency of the acquired interference signal and a signal strength corresponding to the frequency, wherein the second optical path passes the other of the split wavelength-swept light toward the object to be measured as well as the other of the wavelength-swept light reflected from the object to be measured, and the combining element combines the one of the wavelength-swept light that has passed through the first optical path and the other of the wavelength-swept light that has been reflected from the object to be measured and has passed through the second optical path thereby to generate an interference light.

According to the measuring apparatus of the present invention, because the measuring apparatus comprises the wavelength-swept light source apparatus of the present invention, occurrence of the mode hop within the specified period is suppressed during which acquisition of the interference signal used to acquire the position of each part of the object to be measured is carried out. Therefore, occurrence of problems such that the position of each part of the object to be measured becomes difficult to be detected due to the mode hop, or accuracy of the detected position is deteriorated, can be suppressed.

According to the wavelength-swept light source apparatus and the measuring apparatus of the present invention, it is possible to detect occurrence of the mode hop by the mode hop detector, and, when the mode hop occurs within the specified period, to perform the control to change at least one of the occurrence timing of the mode hop and the specified period, thereby to suppress occurrence of the problems due to the mode hop, even if a light source in which a mode hop occurs is used.

BRIEF DESCRIPTION OF THE DRAWINGS

FIGS. 5A-5C are graph showing a relation between intensity of light emitted to the light receiving element and time, in which FIG. 5A shows a state in which a mode hop has not occurred, FIG. 5B shows a state in which a mode hop has occurred within an acquisition period, and FIG. 5C shows a state in which a mode hop has occurred outside of the acquisition period.

FIG. 8A is a graph showing a relation between intensity of light emitted to the light receiving element according to a second modification of the first embodiment of the present invention and time, in which FIG. 8A shows a state in which a mode hop has occurred within an acquisition period.

FIG. 11A is a graph showing a relation between intensity and frequency of light emitted to a light receiving element, in which FIG. 11A shows state in which a mode hop has not occurred.

FIG. 13A is a graph showing a relation between intensity of an interference signal output from the light receiving element and time, in which FIG. 13A shows state in which a mode hop has not occurred or a state in which a mode hop has occurred outside of the acquisition period.

FIG. 14A is a graph showing a relation between intensity and frequency of an interference signal output from a photodetector according to a modification of the third embodiment of the present invention, in which FIG. 14A shows state in which a mode hop has not occurred or a state in which a mode hop has occurred outside of the acquisition period.

DETAILED DESCRIPTION OF THE PREFERRED EMBODIMENTS

First Embodiment

Figure 1:
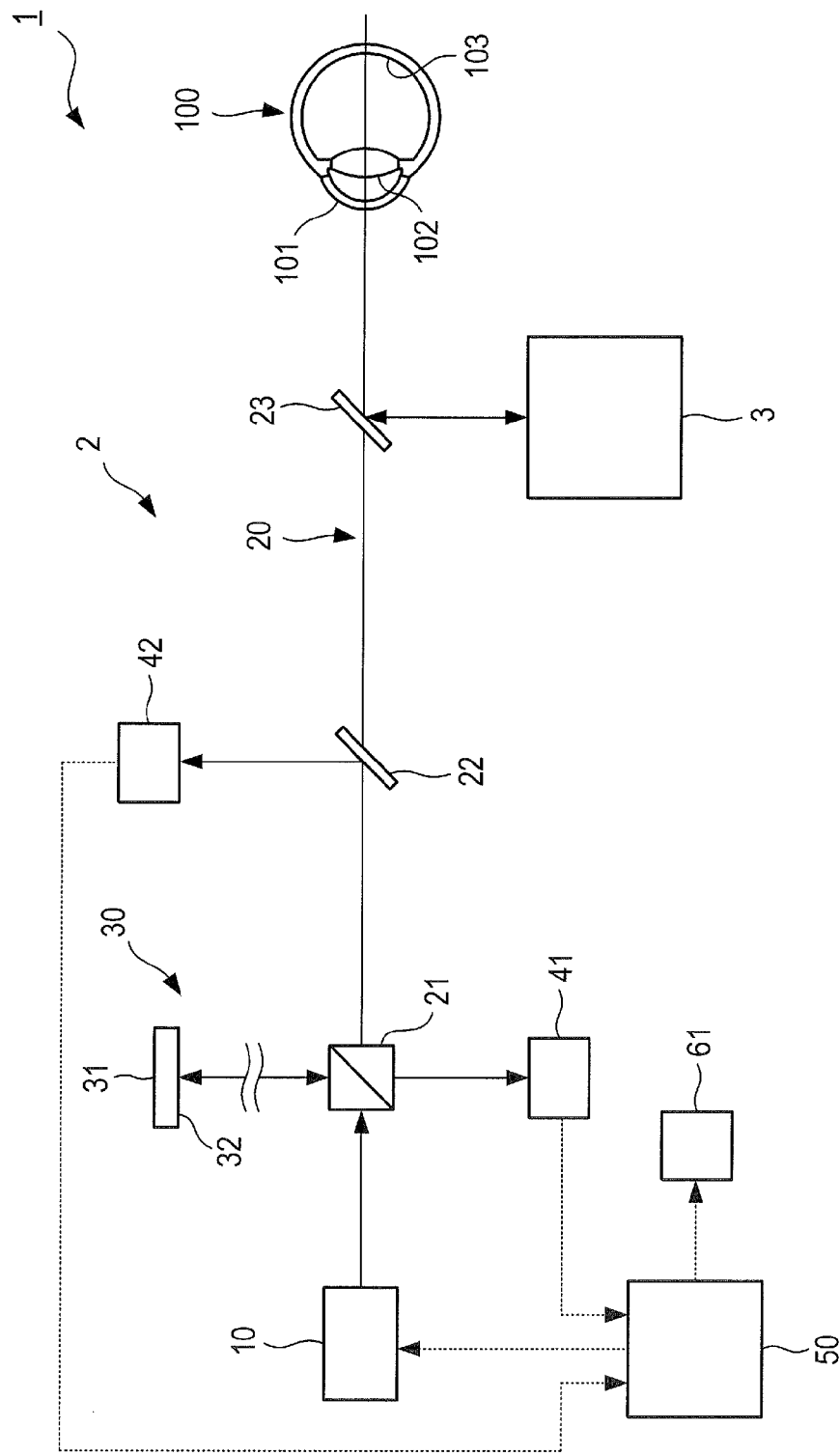
FIG. 1 is a schematic diagram illustrating a configuration of an ophthalmic apparatus according to a first embodiment of the present invention.

Hereinafter, an ophthalmologic apparatus (measuring apparatus) 1 according to a first embodiment of the present invention will be described with reference to FIGS. 1 to 5A-5C. In this embodiment, a description will be given by applying the wavelength-swept light source apparatus and the measuring apparatus of the present invention to the ophthalmologic apparatus 1 that measures an ocular axial length and so on of a subject's eye (object to be measured) 100. More specifically, positions or the like of a cornea 101, a crystalline lens 102 and a retina 103, all of which are regions of the subject's eye 100, are identified. The ocular axial length and so on is determined from the identified results.

The ophthalmologic apparatus 1, as shown in FIG. 1, is mainly composed of an interference optical system 2 that causes a reflected light reflected from the subject's eye 100 to interfere with a reference light, an observation optical system 3 that observes an anterior segment of the subject's eye 100, and a control unit 50 that controls the ophthalmologic apparatus 1.

The interference optical system 2 is comprised mainly of a light source 10 that emits a light of which wavelength is swept, a measurement optical system (second optical path) 20 that radiates the light emitted from the light source 10 to the subject's eye 100 as well as guides the light reflected from the subject's eye 100, and a reference optical system (first optical path) 30 that radiates the light emitted from the light source 10 to a reference surface 32 as well as guides the light reflected from the reference surface 32, a light receiving element 41 that receives a measurement interference light obtained by combining the reflected light guided by the measurement optical system 20 and the reflected light guided by the reference optical system 30, and a light intensity sensor (mode hop detector) 42 that detects intensity of light radiated onto the subject's eye 100.

Figure 2:
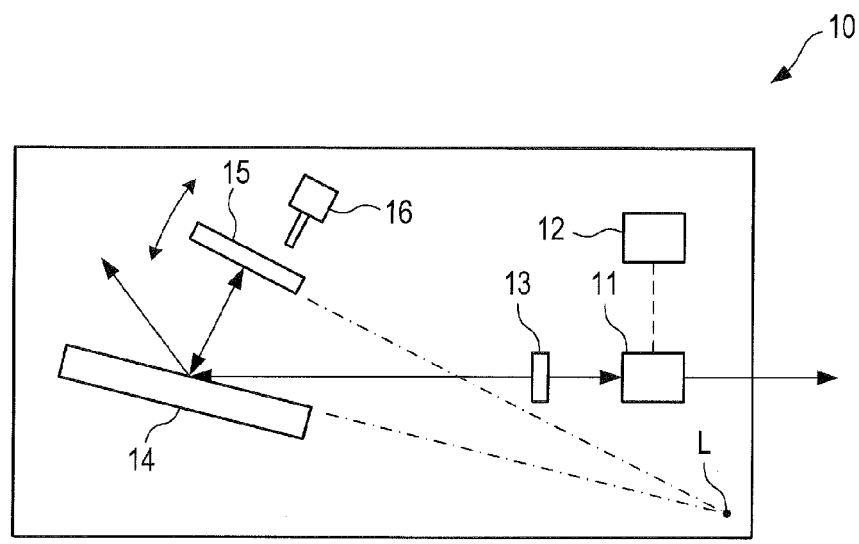
FIG. 2 is a schematic diagram illustrating a configuration of a light source apparatus of FIG. 1.

The light source 10 emits a light used in measurements of the subject's eye 100, of which wavelength is swept at a predetermined cycle. The light source 10, as shown in FIG. 2, is comprised mainly of a light emitting element 11, a drive unit 12, a collimator lens 13, a diffraction grating (wavelength sweep unit) 14, and a wavelength sweep mirror (wavelength sweep unit) 15, and an actuator 16.

The light-emitting element 11 is an element that emits a light having a predetermined wavelength. In this embodiment, the light-emitting element 11 will be described as a semiconductor laser element for an example. The drive unit 12 supplies an injection current to the light emitting element 11. The amount of light emitted from the light emitting element 11 varies depending on a current value of the supplied injection current. The drive unit 12 receives a control signal for controlling the current value of the injection current from the control unit 50. The drive unit 12 controls the injection current supplied based on the input control signal.

The collimator lens 13 is disposed between the light emitting element 11 and the diffraction grating 14. The collimating lens 13 is an element that guides the light emitted from the light emitting element 11 to the diffraction grating 14 and guides the light reflected on the wavelength sweep mirror 15 to the light-emitting element 11 through the diffraction grating 14.

The light emitted from the light emitting element 11 is incident to the diffraction grating 14 at a predetermined incident angle. Some of the incident light is made incident on the wavelength sweep mirror 15 as diffracted light. The light reflected by the wavelength sweep mirror 15 is again incident to the diffraction grating 14. Some of the light incident here is incident to the light-emitting element 11 as diffracted light. The collimating lens 13 and the diffraction grating 14 to be used may be known collimating lenses and diffraction gratings, respectively, and are not limited in particular in terms of form, and so on.

The wavelength sweep mirror 15 is a mirror configured to rotate around an axis L, and is disposed to face the diffraction grating 14. By rotation of the wavelength sweep mirror 15, a distance between the diffraction grating 14 and the wavelength sweep mirror 15 varies periodically. Accordingly, a resonator length that is an optical path length from the light emitting element 11 to the wavelength sweep mirror 15 periodically changes, and the wavelength of light emitted from the light source 10 is periodically swept.

The actuator 16 rotates the wavelength sweep mirror 15 around the axis L, and resonates the wavelength sweep mirror 15 by applying a force to push the wavelength sweep mirror 15 in accordance with a natural frequency on the rotation of the wavelength sweep mirror 15. The actuator 16 receives a control signal from the control unit 50. On the basis of the control signal, the cycle of applying the force to push the wavelength sweep mirror 15, the magnitude and the length of the pushing force, etc. are controlled.

In the present embodiment, a description is given in which, by rotating the wavelength sweep mirror 15 with respect to the diffraction grating 14, the resonator length is periodically changed thereby to periodically sweep the wavelength of the emitted light. Alternatively, the wavelength of the emitted light may be periodically swept by rotating the diffraction grating 14 with respect to the wavelength sweep mirror 15. In this case, the actuator 16 applies a force to push the diffraction grating 14 in accordance with a natural frequency on the rotation of the diffraction grating 14.

The light source 10 is not limited in particular in terms of form, and may be a MEMS type light source with the above-described configuration, or may be a VCSEL (Vertical Cavity Surface Emitting Laser) type light source as long as the wavelength is swept and a mode hop MH occurs.

The measurement optical system 20, as shown in FIG. 1, is comprised mainly of a beam splitter (light splitting element, combining element) 21, a beam splitter 22, and a hot mirror 23. The reference optical system 30 is comprised mainly of the beam splitter 21, and a reference mirror 31.

The beam splitter 21 is an optical element disposed between the light source 10 and the subject's eye 100. The beam splitter 21 reflects part of the light emitted from the light source 10 toward the reference mirror 31 as well as transmits the rest of the light towards the subject's eye 100. Also, the beam splitter 21 combines the reflected light reflected from the subject's eye 100 and the reflected light reflected from the reference mirror 31 to form a measurement interference light. The combined measurement interference light is received by the light receiving element 41.

The beam splitter 22 is an optical element disposed between the beam splitter 21 and the subject's eye 100. The beam splitter 22 reflects part of the light transmitted through the beam splitter 21 and radiated onto the subject's eye 100 toward the light intensity sensor 42 as well as transmits the rest of the light toward the subject's eye 100. The beam splitter 22 also transmits and guides the reflected light reflected from the subject's eye 100 to the beam splitter 21.

The hot mirror 23 is an optical element disposed between the beam splitter 22 the subject's eye 100 and transmits the light transmitted through the beam splitter 22 and reflected on the subject's eye 100. The hot mirror 23 also reflects an observation light used in the observation optical system 3 which will be described later.

Known optical elements can be used as the beam splitter 21, the beam splitter 22 and the hot mirror 23 as long as the optical elements can implement the above features, and are not identified in particular.

The reference mirror 31 is provided with the reference surface 32 onto which the light reflected by the beam splitter 21 is radiated. The light reflected on the reference surface 32 is combined with the reflected light reflected on the subject eye 100 by the beam splitter 21 to generate a measurement interference light.

The light-receiving element 41 is an element that receives the measurement interference light combined by the beam splitter 21 and detects an interference light of the measurement interference light. The light-receiving element 41 also outputs to the control unit 50 a detection signal corresponding to the interference light intensity of the measurement interference light.

The light emitted from the light source 10 is radiated to the light intensity sensor 42 through the beam splitter 22. The light intensity sensor 42 is a sensor that detects the light emitted from the light source 10. The light intensity sensor 42 also outputs toward the control unit 50 a detection signal corresponding to the light intensity (light amount) of the reflected light. The light intensity sensor 42, as described below, is a sensor that is used to detect the mode hop MH in the light source 10 as well as that measures a time mean value of the light radiated onto the subject's eye 100.

Known devices and sensors can be used as the light receiving element 41 and the light intensity sensor 42, such as a photodiode and a pyroelectric detector that outputs a detection signal of which voltage, etc. changes according to the light intensity of the received light. In the present embodiment, a case will be described in which the receiving element 41 and the light intensity sensor 42 are photodiodes as an example.

The observation optical system 3 is used for observation of an anterior segment of the subject eye 100. The observation optical system 3, through the hot mirror 23, radiates the observation light onto the subject's eye 100 and shoots the observation light reflected from the subject's eye 100. As the observation optical system 3, an optical system used in a known ophthalmic apparatus can be used. In this embodiment, detailed description thereof will be omitted.

Figure 3:
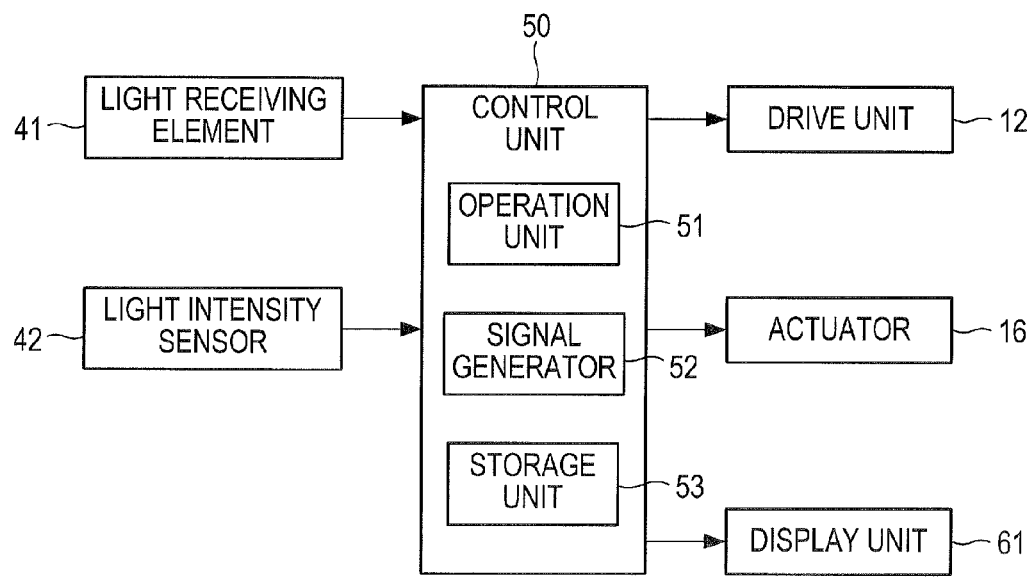
FIG. 3 is a block diagram illustrating a configuration of a control unit of FIG. 1.

The control unit 50 controls each unit in the ophthalmologic apparatus 1. The control unit 50 comprises a CPU (central processing unit), an input and output interface, storage media such as a ROM and a RAM, various drive circuits and detection circuits, and so on. The storage media, as shown in FIG. 3, store, for example, a program that makes the CPU function as an operation unit (analyzing unit) 51 described later and a signal generator 52, and a program that makes the storage media function as a storage unit 53 described later. Since hardware configurations of these units are well known, detailed description thereof will be omitted in the present embodiment.

The control unit 50 receives a detection signal output from the light receiving element 41 and a detection signal output from the light intensity sensor 42. From the control unit 50, a control signal to change the injection current to the light emitting element 11 is output to the drive unit 12, and a control signal to adjust a resonant state of the wavelength sweep mirror 15 is output to the actuator 16. Furthermore, an image signal to be displayed on the display unit 61 is output.

The operation unit 51, based on the detection signal output from the light receiving element 41, identifies a position of each part (front and rear surfaces of the cornea 101, front and rear surfaces of the lens 102 and the surface of the retina 103) of the subject's eye 100, and obtains the ocular axial length of the subject's eye 100 by calculation based on the positions.

The operation unit 51, based on the detection signal output from the light intensity sensor 42, detects the mode hop MH of the wavelength-swept light emitted from the light source 10, and controls the mode hop MH not to occur or exist within an acquisition period (specified period) SP of the interference signal to be used upon obtaining the ocular axial length of the subject's eye 100.

The signal generator 52 is designed to generate an image signal that makes the display unit 61 display information, etc. of the axial length obtained by the operation unit 51, as well as to generate a control signal that makes the drive unit 12 change the injection current when the mode hop MH occurs within the acquisition period SP.

Now, a method for measuring the ocular axial length of the ophthalmologic apparatus 1 configured as above will be explained. Thereafter, a feature of the present embodiment, that is, how to control the occurrence of the mode hop MH will be described. First, as shown in FIG. 1, alignment of the ophthalmic apparatus 1 is performed with respect to the subject's eye 100. Since the alignment to be performed is the same as what is generally performed, detailed description thereof will be omitted in the present embodiment.

When the alignment is done, the wavelength-swept light emitted from the light source 10 is radiated onto the subject's eye 100, and acquisition of the interference signal detected by the light receiving element 41 is performed. The acquisition period SP to acquire an interference signal is set to match a period during which time variation of the wavelength in the wavelength-swept light is linear. More specifically, based on a clock signal generated by the control unit 50 and used for synchronization, the cycle of the wavelength in the wavelength-swept light and the acquisition timing are set so as to maintain the relation described above.

Figure 4A:
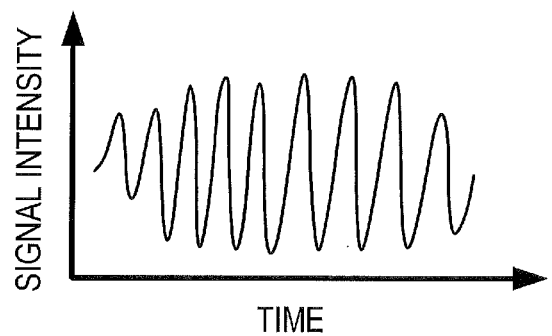
FIG. 4A is a graph showing a relation between a detected signal strength of a light receiving element and time.

The measurement interference light received by the light receiving element 41 comprises a light reflected from each part in a depth direction of the subject's eye 100. Therefore, the interference signal detected by the light receiving element 41, as shown in FIG. 4A, is a signal of which intensity varies over time. The interference signal comprises a signal of the interference light obtained by combining the light reflected from each part of the subject's eye 100 (front and rear surfaces of the cornea 101, the front and rear surfaces of the lens 102, and the surface of the retina 103) and the reference light.

Figure 4B:
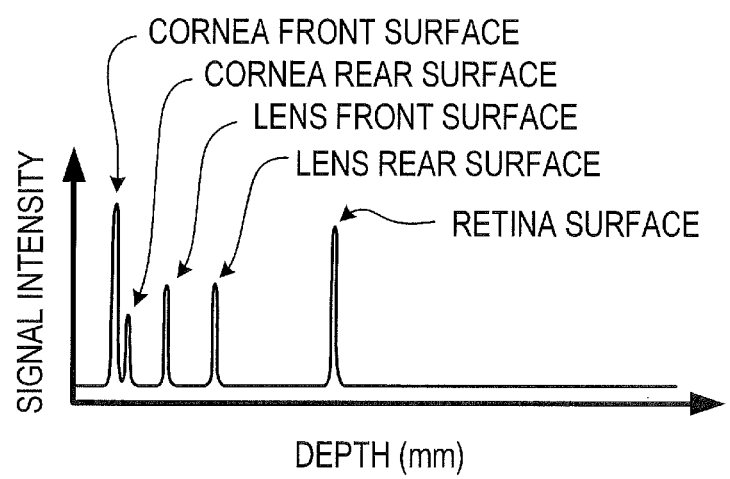
FIG. 4B is a graph showing a relation between a signal strength and a depth after the Fourier transform.

The operation unit 51 of the control unit 50 performs an arithmetic process of Fourier transform of the interference signal as described above. This process, as shown in FIG. 4B, separates signal components of the reflected light reflected from each part of the subject's eye 100 (front and rear surfaces of the cornea 101, front and rear surfaces of the lens 102, and surface of the retina 103). Based on the separated signal components, it becomes possible to identify the position of each part of the subject's eye 100.

Thereafter, the operation unit 51, based on the identified position of each part of the subject's eye 100, performs an arithmetic process of obtaining the ocular axial length (length from the anterior surface of the cornea 101 to the surface of the retina 103) of the subject's eye 100. Specifically, the position of the anterior surface of the cornea 101 of the subject's eye 100 is subtracted from the position of the surface of the retina 103. Thereby, the ocular axial length of the subject's eye 100 based on the interference light is calculated.

Part of the wavelength-swept light emitted from the light source 10 is radiated to the light intensity sensor 42 through the beam splitter 22. The light intensity sensor 42 outputs a detection signal corresponding to the light intensity of the received light. The operation unit 51 of the control unit 50, based on the input detection signal, calculates the time mean value in the light amount of the light radiated onto the subject's eye 100. The calculated time mean value is compared with the previously stored standard value in the storage unit 53, and is used to manage the light amount of the light radiated onto the subject's eye 100. The detection signal output from the light intensity sensor 42 is also used to detect the mode hop MH in the light source 10.

The feature of the present embodiment, that is, how to control the occurrence of the mode hop MH will now be described.

Figure 5A:
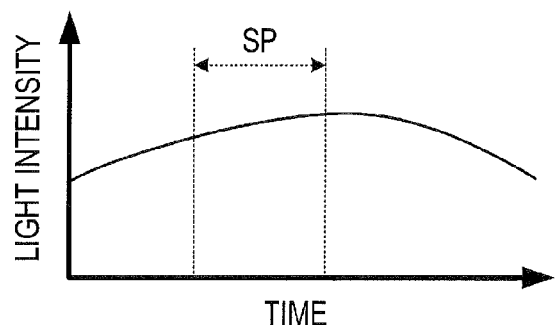
Figure 5B:
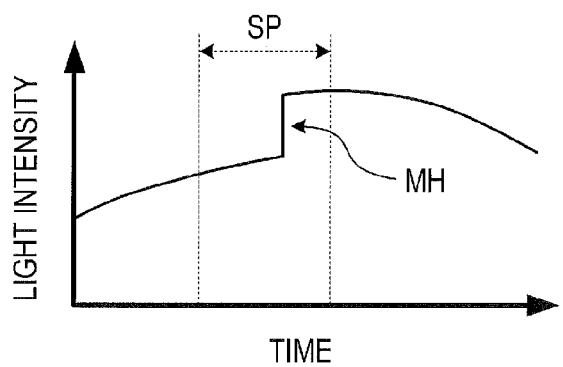
Figure 5C:
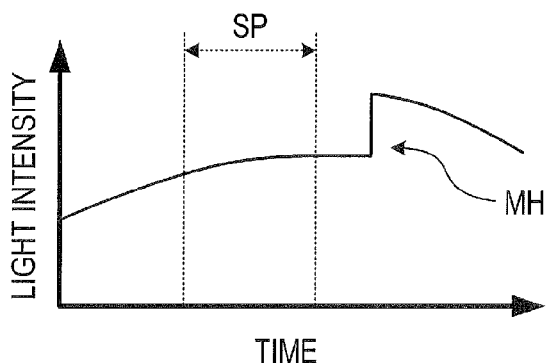

When the wavelength-swept light is emitted from the light source 10, the detection signal corresponding to the light intensity of the wavelength-swept light detected by the light intensity sensor 42 is input to the operation unit 51, as described above. The operation unit 51 acquires a relation between the time and the light intensity as shown in FIGS. 5A to 5C. The operation unit 51 detects presence or absence of the mode hop MH based on the acquired relation, and further determines whether the mode hop MH has occurred within the acquisition period SP.

FIGS. 5A to 5C further show the acquisition period SP in an overlapped manner. FIG. 5A shows a state in which the mode hop MH has not occurred in the wavelength-swept light. Therefore, the mode hop MH has not occurred also within the acquisition period SP. On the other hand, in FIG. 5B, the mode hop MH has occurred in the wavelength-swept light, and shows a state in which the mode hop MH has occurred within the acquisition period SP. Also, FIG. 5C shows a state in which the mode hop MH has occurred in the wavelength-swept light but outside of the acquisition period SP.

The operation unit 51, if it determines that the relation between the time and the light intensity is in a state in which the mode hop MH has occurred in the wavelength-swept light shown in FIG. 5B and within the acquisition period SP, performs a control to move the mode hop MH outside of the acquisition period SP. Specifically, a control signal to change the value of the injection current to be supplied to the light emitting element 11 by a predetermined value is output from the control unit 50 to the drive unit 12 of the light source 10.

Change of the value of the injection current can be a change to increase the current value by a predetermined value, or may be a change to reduce the current value by a predetermined value. When the value of the injection current is changed, the occurrence timing of the mode hop MH is moved, and the mode hop MH moves outside of the acquisition period SP. For example, the mode hop MH that has occurred at the timing shown in FIG. 5B is moved to a timing shown in FIG. 5C). The direction of the mode hop MH to move may be right or left in FIGS. 5A to 5C.

In the state in which the relation between the time and the light intensity is as shown in FIG. 5A or 5C, the control unit 50 does not perform a control to move the timing of the mode hop MH, that is, a control to change the value of the injection current to be supplied to the light emitting element 11 by a predetermined value.

According to the ophthalmologic apparatus 1 configured as above, occurrence of the mode hop MH is suppressed within the acquisition period SP during which the acquisition of the interference signal used upon determining the position of each part of the subject's eye 100 is made. Thus, occurrence of defects due to a mode hop is suppressed, such that it becomes difficult to detect the position of each part of the subject's eye 100 due to the mode hop MH or that accuracy of the detected position is deteriorated.

When the mode hop MH occurs in the wavelength-swept light emitted from the light source 10, the occurrence is detected by the light intensity sensor 42. The control unit 50, when the mode hop MH occurs within the acquisition period SP, performs a control to change the occurrence timing of mode hop MH. As a result, the mode hop MH is to occur or exist outside of the acquisition period SP. In other words, occurrence or existence of the mode hop MH within the acquisition period SP is suppressed.

By detecting the light intensity of the emitted wavelength-swept light by the light intensity sensor 42, it is possible to indirectly detect the wavelength of the wavelength-swept light. In other words, because the wavelength and the light intensity in the wavelength-swept light are in one-to-one relation, the wavelength can be known by detecting the light intensity. Detection of the mode hop MH is also possible even when the mode hop MH occurs outside of the acquisition period SP. Therefore, it becomes possible to prevent the effect of the mode hop MH from appearing in the measurement results of the ophthalmologic apparatus 1. In addition, if a light intensity sensor for measuring a time mean value of the light radiated onto the subject's eye 100 is present, it is possible to share the sensor and reduce the number of components.

By controlling the injection current to be supplied to the light emitting element 11, the occurrence timing of the mode hop MH in the wavelength-swept light emitted from the light source 10 varies. Therefore, a relation between the acquisition period SP and the occurrence timing of the mode hop MH described above varies. Thereby, occurrence or existence of the mode hop MH within the acquisition period SP is suppressed.

The control of the injection current is not limited in particular, and may be a control to change the current value only by a predetermined given value as in the embodiment described above, or may be a control to adjust the current value that changes according to the timing at which the mode hop MH occurs just like a feedback control.

First Modification of First Embodiment

A first modification of the first embodiment of the present invention will be described with reference to FIGS. 6 and 7. Although the basic configuration of the ophthalmologic apparatus of the present modification is the same as that of the first embodiment, the control method of moving a mode hop is different from that of the first embodiment. Therefore, in this modification, a description will be given only about of the movement of the mode hop with reference to FIGS. 6 and 7, and a description of the other components, etc. is not repeated.

Figure 6:
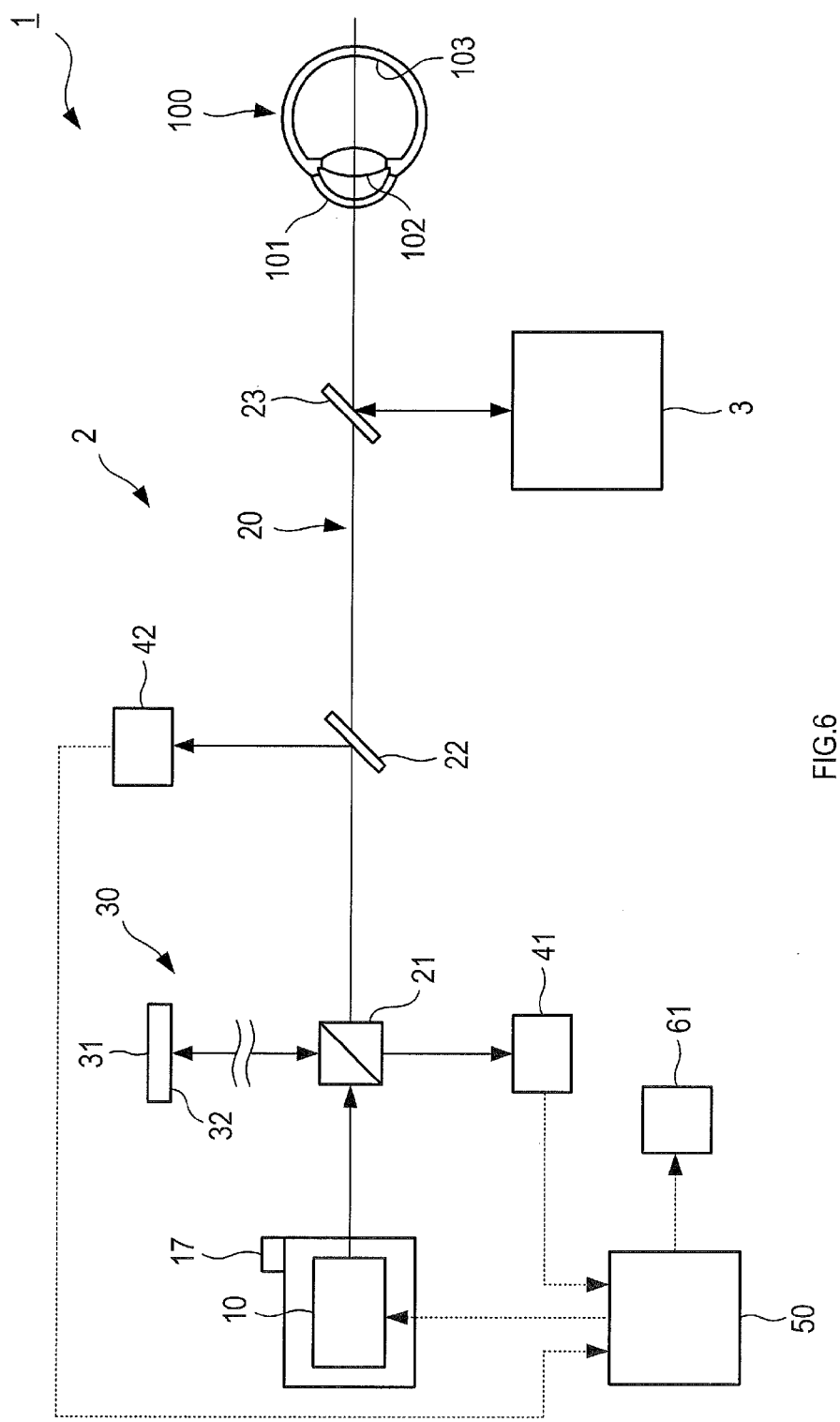
FIG. 6 is a schematic diagram illustrating a configuration of an ophthalmic apparatus according to a first modification of the first embodiment of the present invention.
Figure 7:
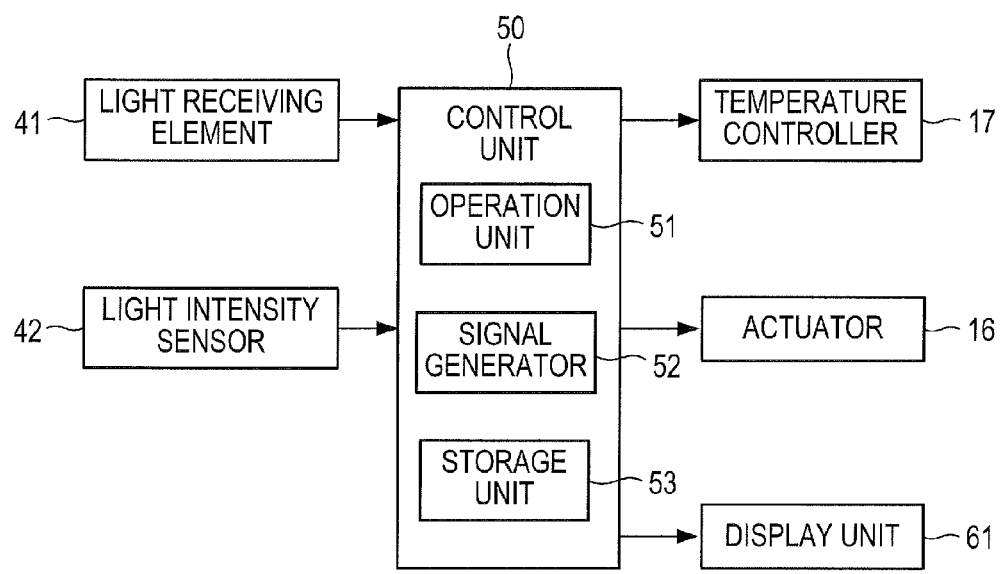
FIG. 7 is a block diagram illustrating a configuration of a control unit of FIG. 6.

The light source 10 of the ophthalmologic apparatus 1 of this modification further comprises a temperature controller 17, as shown in FIG. 6. The temperature controller 17 adjusts the temperature of the light emitting element 11 in the light source 10. The temperature controller 17, as shown in FIG. 7, receives a control signal for temperature adjustment from the control unit 50. The temperature controller 17 adjusts the temperature based on the received control signal.

In this embodiment, an example provided with a housing for covering the light source 10 and the controller for adjusting the temperature inside of the housing is illustrated. The configuration of the temperature controller 17 is not limited to the illustrated one. Those having other known configurations may be also used.

Now, how to control the occurrence of the mode hop MH, which is a feature of this modification, will be described. Since the measurement method of the ocular axial length is the same as that of the first embodiment, a description thereof is not to be repeated.

When the wavelength-swept light is emitted from the light source 10, the operation unit 51, as in the first embodiment, detects presence or absence of the mode hop MH based on the obtained relation, and further determines whether the mode hop MH has occurred within the acquisition period SP.

The operation unit 51, if it determines that the relation between the time and the light intensity is in a state in which the mode hop MH has occurred in the wavelength-swept light shown in FIG. 5B and within the acquisition period SP, performs a control to move the mode hop MH outside of the acquisition period SP. Specifically, a control signal for changing the temperature of the light emitting element 11 by a predetermined value is output from the control unit 50 to the temperature controller 17.

Temperature changes of the light emitting element 11 can be a change to increase the temperature by a predetermined value, or may be a change to decrease the temperature by a predetermined value. When the temperature of the light emitting element 11 is changed to move the occurrence timing of the mode hop MH, the mode hop MH moves outside of the acquisition period SP. For example, the mode hop MH that occurs at the timing shown in FIG. 5B is moved to the timing shown in FIG. 5C. The direction of movement of the mode hop MH may be right or left in FIGS. 5A to 5C.

It is the same as in the first embodiment that, when the relation between the time and the light intensity is in the state shown in FIG. 5A or 5C, the control unit 50 does not perform the control to move the timing of the mode hop MH.

According to the ophthalmologic apparatus 1 configured as above, by controlling the temperature of the light emitting element 11, the occurrence timing of the mode hop MH in the wavelength-swept light emitted from the light source apparatus 10 varies. Therefore, the relation between the acquisition period SP and the occurrence timing of the mode hop MH described above varies, and occurrence or existence of the mode hop MH within the acquisition period SP is suppressed.

Second Modification of First Embodiment

A second modification of the first embodiment of the present invention will now be described with reference to FIGS. 8A and 8B. Although the basic configuration of the ophthalmologic apparatus of the present modification is the same as that of the first embodiment, the way of varying the relation between the acquisition period and the occurrence timing of the mode hop is different from that of the first embodiment. Thus, in this modification, a description will be given only about the way of varying the relation with reference to FIGS. 8A and 8B, and a description for the other components, etc. is not repeated.

Here, a description will be given on a control to vary the relation between the acquisition period SP and the occurrence timing of the mode hop MH, which is a feature of this modification. The configuration of the ophthalmologic apparatus 1 of the present modification and the measurement method of the ocular axial length are the same as those of the first embodiment, and thus a description thereof is not repeated.

When the wavelength-swept light is emitted from the light source 10, the operation unit 51, as in the first embodiment, detects presence or absence of the mode hop MH based on the obtained relation, and further determines whether the mode hop MH has occurred within the acquisition period SP.

Figure 8A:
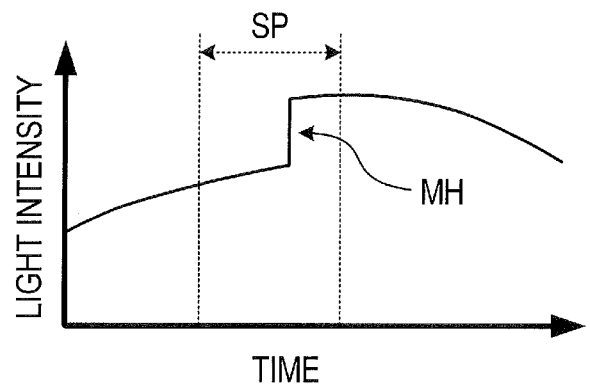
Figure 8B:
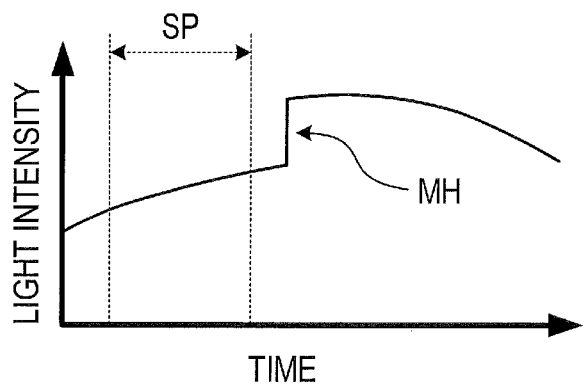
FIG. 8B shows a state in which a mode hop has occurred outside of the acquisition period.

The operation unit 51, if it determines that the relation between the time and the light intensity is in a state in which the mode hop MH has occurred in the wavelength-swept light and within the acquisition period SP, as shown in FIG. 8A, performs a control to move the mode hop MH outside of the acquisition period SP by moving the timing of the acquisition period SP.

Specifically, a control is performed to change the starting point of the acquisition period SP for the clock signal. FIG. 8B shows a state in which, by advancing the starting point of the acquisition period SP (moving to the left in the figure), the relation between the acquisition period SP and the occurrence timing of the mode hop MH varies, and the mode hop MH occurs outside of the specified period SP.

Change of the starting point within the acquisition period SP can be a change to hasten the starting point as described above, or may be a change to slow the starting point (move to the right in the figure). It is the same as in the first embodiment that, when the relation between the time and the light intensity is in the state shown in FIG. 5A or 5C, the control unit 50 does not perform the control to move the timing of the mode hop MH.

According to the ophthalmologic apparatus 1 configured as above, by controlling the relative position of the acquisition period SP to the occurrence timing of the mode hop MH, the relation between the acquisition period SP and the occurrence timing of the mode hop MH described above varies, and occurrence or existence of the mode hop MH within the acquisition period SP is suppressed.

Note that the control of the relative position of the acquisition period SP may be performed in the control of the starting point of the acquisition period SP as described above, or may be performed in control of the end point, the time length of the acquisition period SP, or the combination thereof. The control of the time length of the period is, for example, a control to shorten the time length of the acquisition period SP when the occurrence of the mode hop MH is detected within the acquisition period SP. As a result of this control, the mode hop MH is to occur outside of the acquisition period SP.

Third Modification of First Embodiment

A third modification of the first embodiment of the present invention will now be described with reference to FIGS. 2 to 5A-5C. Although the basic configuration of the ophthalmologic apparatus of the present modification is the same as that of the first embodiment, the control method of moving a mode hop is different from that of the first embodiment. Therefore, in this modification, a description will be given only about of the movement of the mode hop with reference to FIGS. 2 to 5A-5C, and a description of the other components, etc. is not repeated.

Here, a description will be given on a control to move the mode hop MH which is a feature of this modification. The configuration of the ophthalmologic apparatus 1 of the present modification and the measurement method of the axial length are the same as those of the first embodiment, and thus the description thereof is not repeated.

When the wavelength-swept light is emitted from the light source 10, the operation unit 51, as in the first embodiment, detects the presence or absence of the mode hop MH based on the obtained relation, and further determines whether the mode hop MH has occurred within the acquisition period SP.

The operation unit 51, if it determines that the relation between the time and the light intensity is in a state in which the mode hop MH has occurred in the wavelength-swept light shown in FIG. 5B and within the acquisition period SP, performs a control to move the mode hop MH outside of the acquisition period SP. Specifically, a control signal for changing a resonance state of the wavelength sweep mirror 15, that is one of the wavelength sweep characteristics, is output from the control unit 50 to the actuator 16. The wavelength sweep characteristics may be anything as long as it involves a change in the relation of the relative positions between the wavelength sweep mirror 15 and the diffraction grating 14, and are not limited to the change in the resonance state of the wavelength sweep mirror 15.

Specifically, by changing the cycle to apply a pushing force to the wavelength sweep mirror 15, or the magnitude or the length of the pushing force, a vibration state of the wavelength sweep mirror 15 in the resonant state is changed. Along with this, the width of the wavelength variation in the wavelength-swept light emitted from the light source 10 and the variation cycle vary.

When the width of wavelength variation in the wavelength-swept light and the variation cycle are changed, the occurrence timing of the mode hop MH moves, and moves outside of the acquisition period SP. For example, the mode hop MH that has occurred at the timing shown in FIG. 5B moves to the timing shown in FIG. 5C.

According to the ophthalmologic apparatus 1 configured as above, by controlling the movement of the wavelength sweep mirror 15, the width of the wavelength variation in the wavelength-swept light emitted from the light source 10 and the variation cycle vary. As a result of this change, the occurrence timing of the mode hop MH in wavelength-swept light also varies. Therefore, the relation between the acquisition period SP and the occurrence timing of the mode hop MH described above varies, and occurrence or existence of the mode hop MH within the acquisition period SP is suppressed.

In the case where the light source 10 is employed having a configuration in which the wavelength of the emitted light is periodically swept as the diffraction grating 14 rotates with respect to the wavelength sweep mirror 15, a control to move the mode hop MH outside of the acquisition period (SP) is performed by outputting a control signal for changing the position of the diffraction grating 14, that is one of the wavelength sweep characteristics, from the control unit 50 to the actuator 16.

In the first embodiment described above, and in each variant, an apparatus comprising at least the light source 10, the light intensity sensor 42, and the control unit 50 corresponds to a wavelength-swept light source apparatus in the claims.

Second Embodiment

A description will now be given on a second embodiment of the present invention with reference to FIGS. 9 to 11A-11C. Although the basic configuration of the ophthalmic apparatus of the present embodiment is the same as that of the first embodiment, the method for detecting a mode hop is different from that the first embodiment. Therefore, in this embodiment, a description will be given only about the method for detecting a mode hop with reference to FIGS. 9 to 11A-11C, and a description of the other components, etc. is not repeated.

Figure 9:
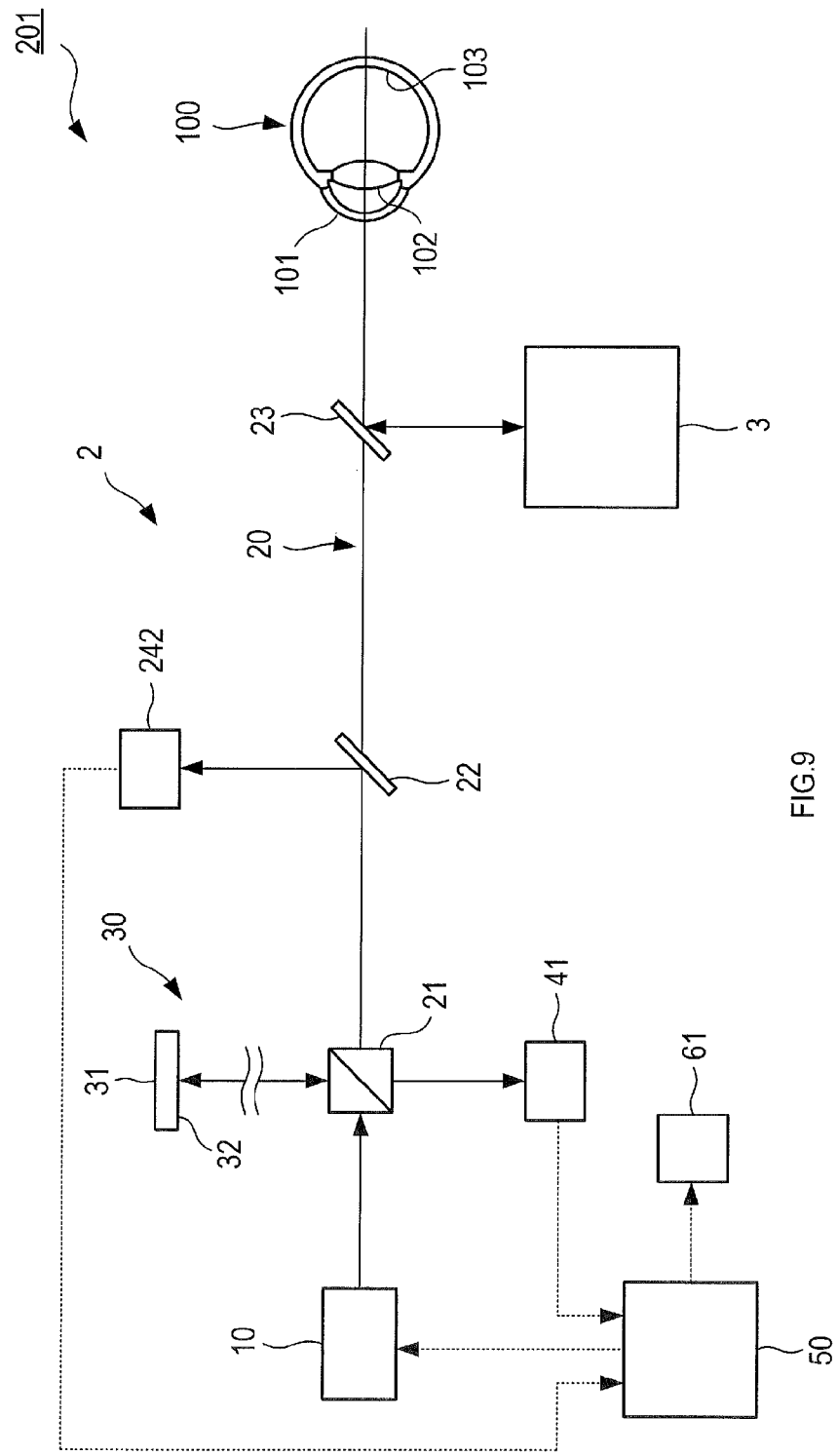
FIG. 9 is a schematic diagram illustrating a configuration of the ophthalmologic apparatus according to a second embodiment of the present invention.
Figure 10:
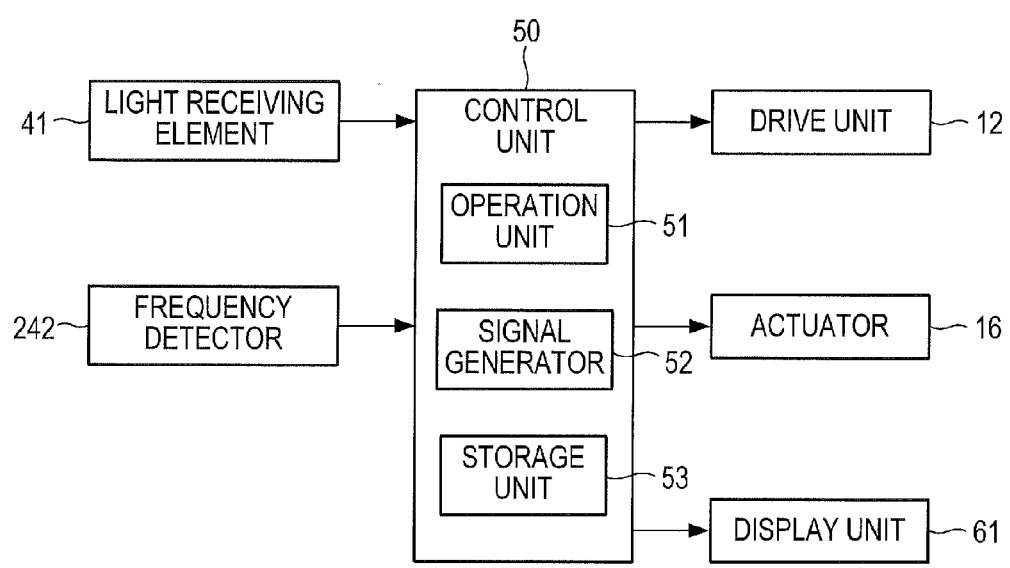
FIG. 10 is a block diagram illustrating a configuration of a control unit of FIG. 9.

An ophthalmic apparatus 201 of the present embodiment, as shown in FIG. 9, is different from that of the first embodiment in that a frequency detector 242 is provided instead of the light intensity sensor 42. The frequency detector 242 receives the light reflected by the beam splitter 22 and detects the wavelength of the reflected light. A detection signal output from the frequency detector 242 is input to the control unit 50. In the present embodiment, a description will be given in which a spectrometer such as a spectrum analyzer is used as the frequency detector 242 for an example.

A description will now be given on a control to move the mode hop MH which is a feature of this embodiment. Since the measurement method of the ocular axial length is the same as that of the first embodiment, a description thereof is not repeated.

Figure 11A:
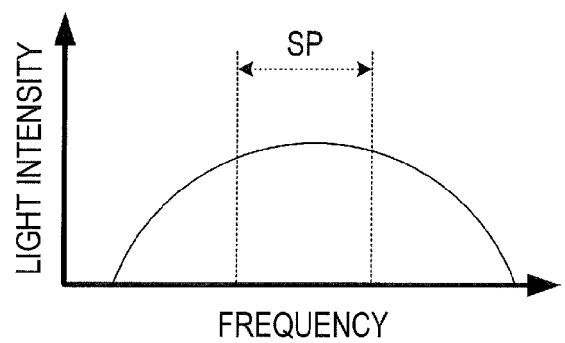
Figure 11B:
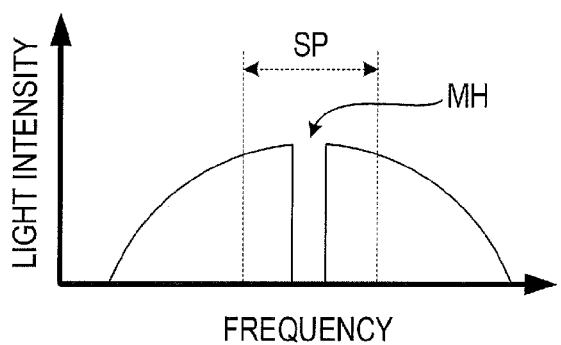
FIG. 11B shows a state in which the mode hop has occurred within an acquisition period.
Figure 11C:
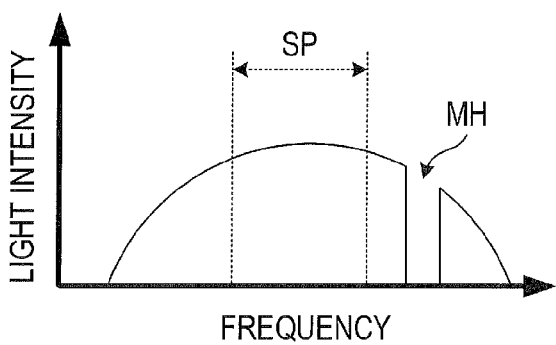
FIG. 11C shows a state in which the mode hop has occurred outside of the acquisition period.

When the wavelength-swept light is emitted from the light source 10, a detection signal corresponding to the frequency of the wavelength-swept light detected by the frequency detector 242 is input to the operation unit (mode hop detector) 51. The operation unit 51, based on the input detection signal, obtains a relation between the frequency and the light intensity as shown in FIGS. 11A to 11C. The operation unit 51 detects presence or absence of the mode hop MH based on the obtained relation, and further determines whether the mode hop MH has occurred within the acquisition period SP.

FIGS. 11A to 11C further show the acquisition period SP in an overlapped manner. FIG. 11A shows a state in which the mode hop MH has not occurred in the wavelength-swept light. Therefore, the mode hop MH has not occurred also within the acquisition period SP. On the other hand, FIG. 11B shows a state in which the mode hop MH has occurred in the wavelength-swept light and within the acquisition period SP. In addition, FIG. 11C shows a state in which the mode hop MH has occurred in the wavelength-swept light but outside of the acquisition period SP.

The operation unit 51, if it determines that the relation between the time and the light intensity is in a state in which the mode hop MH has occurred in the wavelength-swept light as shown in FIG. 11B and within the acquisition period SP, performs a control to move the mode hop MH outside of the acquisition period SP. Specifically, a control signal to change the value of the injection current supplied to the light emitting element 11 by a predetermined value is output from the control unit 50 to the drive unit 12 of the light source 10.

According to the ophthalmologic apparatus 201 configured as above, by using the frequency detector 242, the frequency of the wavelength-swept light can be directly detected. Therefore, it is possible to directly detect the mode hop MH in the wavelength-swept light. The detection is possible even if the mode hop MH occurs outside of the acquisition period SP. Therefore, it becomes possible to prevent the effect of the mode hop MH from appearing in the measurement results of the ophthalmologic apparatus 1.

In the second embodiment described above, an apparatus comprising at least the light source 10, the frequency detector 242 provided instead of the light intensity sensor 42, and a control unit 50 corresponds to the wavelength-swept light source apparatus in the claims.

Third Embodiment

A third embodiment of the present invention will now be described with reference to FIGS. 12 and 13A-13B.

Although the basic configuration of the ophthalmic apparatus of the present embodiment is the same as that of the first embodiment, the method for detecting a mode hop is different from that of the first embodiment. Therefore, in this embodiment, a description will be given only about the method for detecting a mode hop with reference to FIGS. 12 and 13A-13B, and a description of the other components, etc. is not repeated.

Figure 12:
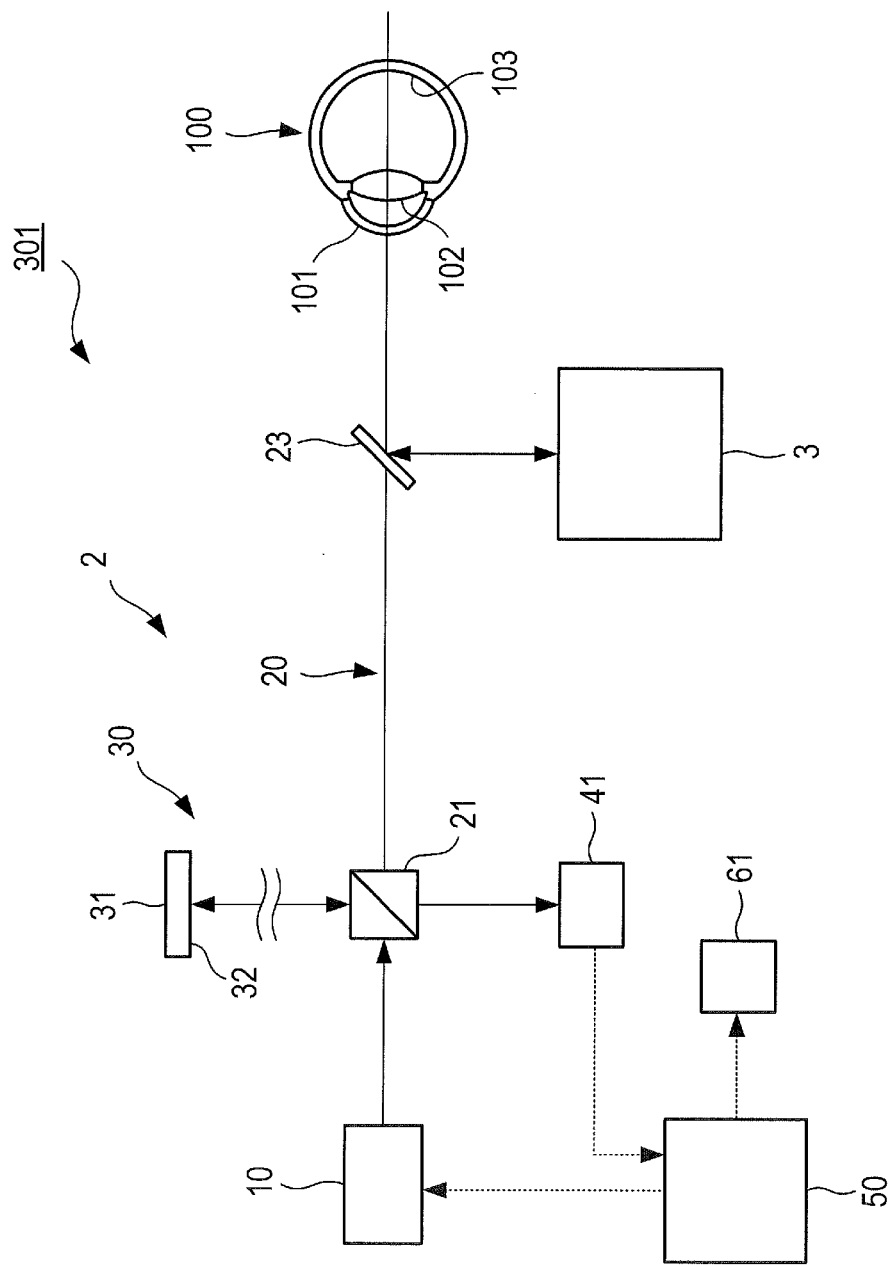
FIG. 12 is a schematic diagram illustrating a configuration of an ophthalmic apparatus according to a third embodiment of the present invention.

An ophthalmic apparatus 301 of the present embodiment, as shown in FIG. 12, is different from that of the first embodiment in that the light intensity sensor 42 is not provided. Thereby, the control for moving the mode hop MH will be as described in the following. Since the measurement method of the ocular axial length is the same as that of the first embodiment, a description thereof is not repeated.

When the wavelength-swept light is emitted from the light source 10, an interference signal (also referred to as a beat signal) based on the measurement interference light detected by the light receiving element 41 is input to the operation unit 51 from the light receiving element 41. The operation unit 51, based on the input interference signal, determines the relation between the time and the intensity of the interference signal, as shown in FIGS. 13A and 13B. The operation unit 51 determines whether the mode hop MH has occurred within the acquisition period SP based on the obtained relation.

Figure 13A:
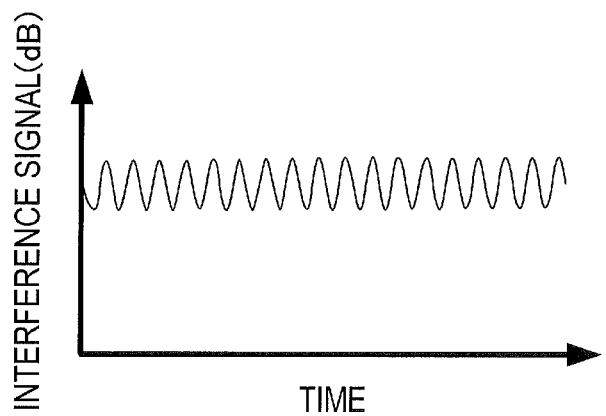

FIG. 13A shows a state in which the mode hop MH has not occurred in the wavelength-swept light, or has occurred outside of the acquisition period (SP). FIG. 13B shows a state in which the mode hop MH has occurred within the acquisition period SP.

Figure 13B:
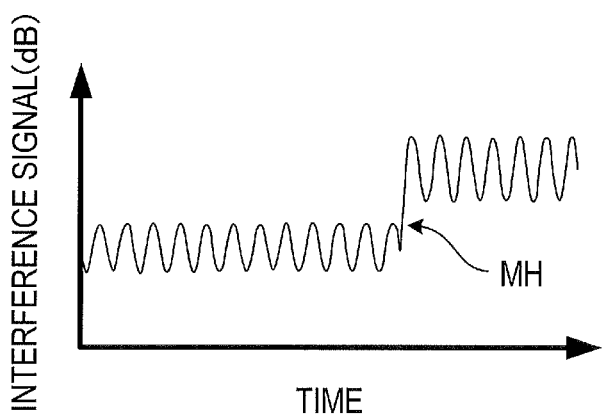
FIG. 13B shows a state in which a mode hop has occurred within the acquisition period.

The operation unit 51, if it determines that the relation between the time and the light intensity is in a state in which the mode hop MH has occurred within the acquisition period SP shown in FIG. 13B, performs a control to move the mode hop MH outside of the acquisition period SP. Specifically, a control signal to change the value of the injection current supplied to the light emitting element 11 by a predetermined value is output from the control unit 50 to the drive unit 12 of the light source 10.

According to the ophthalmologic apparatus 301 configured as above, it is possible to detect that the mode hop MH has occurred within the acquisition period SP, based on the time change of the signal strength in the interference signal. That is, when the mode hop MH has occurred in the wavelength-swept light, the time change of the signal strength in the interference signal becomes discontinuous, as compared with a case where the mode hop MH has not occurred in the wavelength-swept light. By detecting the discontinuous change, it is possible to detect that the mode hop MH has occurred within the acquisition period SP.

In addition, only with the configuration required for the measurement of the subject's eye 100 by the ophthalmologic apparatus 301, it is possible to detect that the mode hop MH has occurred within the acquisition period SP. In other words, without increasing the number of components, the detection can be performed that the mode hop MH has occurred within the acquisition period SP. Downsizing and cost reduction of the ophthalmic apparatus 301 can be easily achieved.

Modification of Third Embodiment

A modification of the third embodiment of the present invention will now be described with reference to FIGS. 14A and 14B. Although the basic configuration of the ophthalmic apparatus of the present modification is the same as that of the third embodiment, the method for detecting a mode hop is different from that of the third embodiment. Thus, in this modification, a description will be given only about the method for detecting a mode hop with reference to FIGS. 14A and 14B, and a description of the other components, etc. is not repeated.

Here, description will be given on a control to move the mode hop MH, which is a feature of this modification. The configuration of the ophthalmologic apparatus 301 of this modification and the measurement method of the ocular axial length are the same as those of the first embodiment, and thus a description thereof is not repeated.

When the wavelength-swept light is emitted from the light source 10, an interference signal (also referred to a beat signal) based on the measurement interference light detected by the light receiving element 41 is input to the operation unit 51 from the light receiving element 41. The operation unit 51, by Fourier transform of the input interference signal, determines the relation between the frequency and the intensity of the interference signal as shown in FIGS. 14A and 14B. The operation unit 51 determines whether the mode hop MH has occurred within the acquisition period SP based on the obtained relation.

Figure 14A:
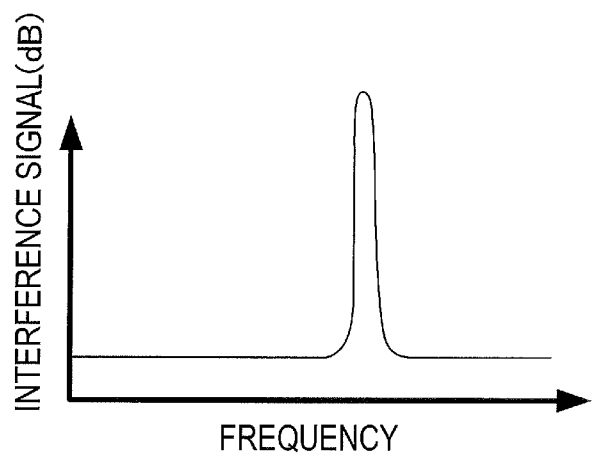

FIG. 14A shows a state in which the mode hop MH has not occurred in the wavelength-swept light, or has occurred outside of the acquisition period SP. In this case, the shape of the peak is relatively simple with one vertex. FIG. 14B shows a state in which the mode hop MH has occurred within the acquisition period SP. In this case, the shape of the peak is relatively complex with a plurality of vertices.

Figure 14B:
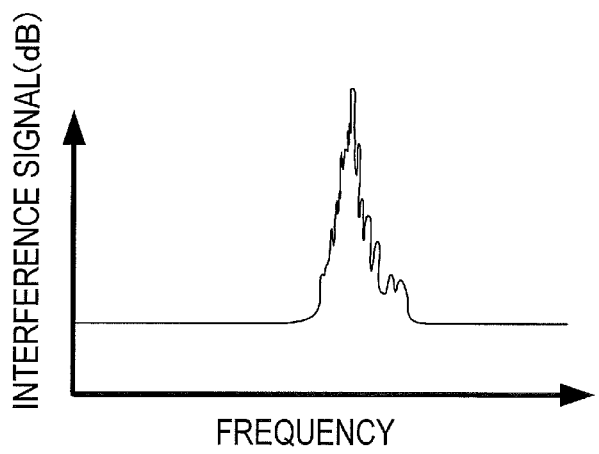
FIG. 14B shows a state in which a mode hop has occurred within the acquisition period.

The operation unit 51, if it determines that the relation between the time and the light intensity is in a state in which the mode hop MH has occurred within the acquisition period SP shown in FIG. 14B, performs a control to move the mode hop MH outside of the acquisition period SP. Specifically, a control signal to change the value of the injection current supplied to the light emitting element 11 by a predetermined value is output from the control unit 50 to the drive unit 12 of the light source 10.

According to the ophthalmologic apparatus 301 having the configuration described above, the detection that the mode hop MH has occurred within the acquisition period SP can be performed based on the shape of the peak in the relation between the frequency in the interference signal and the signal strength corresponding to the frequency. That is, when the mode hop MH has occurred in the wavelength-swept light, the shape of the peak changes, as compared with a case where the mode hop MH has not occurred in the wavelength-swept light. By detecting this change, it is possible to detect that the mode hop MH has occurred within the acquisition period SP.

In the third embodiment described above, an apparatus that comprises at least the light source 10, the beam splitter 21, the measurement optical system 20, the reference optical system 30, the light receiving element 41, and the control unit 50 corresponds to the wavelength-swept light source apparatus in the claims.

It is to be noted that the technical scope of the present invention is not limited to the above embodiments, and various modifications can be made without departing from the scope of the invention. For example, application of the present invention is not limited in particular, and the present invention may be applied not only to the above embodiments but also to appropriate combinations thereof.

In addition, in the above embodiments, although the invention has been applied to the ophthalmic device used for measuring an ocular axial length, the invention is not limited to the ophthalmic apparatus for measuring an ocular axial length, and can be applied to various ophthalmic apparatus utilizing the light of which wavelength is swept.

EXPLANATION OF REFERENCE NUMERALS 1, 201, 301 . . . ophthalmic apparatus (measuring apparatus), 10 . . . light source, 11 . . . light-emitting element, 14 . . . diffraction grating (wavelength sweeping section), 15 . . . wavelength sweep mirror section (wavelength sweeping section), 17 . . . temperature controller, 20 . . . measurement optical system (second optical path), 21 . . . beam splitter (light splitting element, combining element), 30 . . . reference optical system (first optical path), 41 . . . light-receiving element, 42 . . . light intensity sensor (mode hop detector), 51 . . . operation unit (analyzing unit, mode hop detector), 100 . . . subject's eye (object to be measured), 101 . . . cornea (site), 102 . . . lens (site), 103 . . . retina (site), 242 . . . frequency detector, SP . . . acquisition period (specified period), MH . . . mode hop

What is claimed is:

1. A wavelength-swept light source apparatus comprising:
a light source that emits a wavelength-swept light of which wavelength varies in a predetermined cycle;
a mode hop detector that detects a mode hop of the wavelength-swept light emitted from the light source; and
a control unit that controls at least one of a parameter that defines a specified period having a predetermined fixed or variable time length provided in the predetermined cycle and a control parameter of the light source, thereby to set an occurrence timing of the mode hop detected by the mode hop detector outside of the specified period.

2. The wavelength-swept light source apparatus according to claim 1,
wherein the light source comprises a light-emitting element that emits light,
the control unit controls an injection current supplied to the light-emitting element as the control parameter of the light source, thereby to set a timing of the mode hop detected by the mode hop detector outside of the specified period.

3. The wavelength-swept light source apparatus according to claim 1,
wherein the light source comprises a light-emitting element that emits light and a temperature controller that adjusts a temperature of the light emitting element, and
the control unit controls the temperature of the light emitting element by the temperature controller as the control parameter of the light source, thereby to set a timing of the mode hop detected by the mode hop detector outside of the specified period.

4. The wavelength-swept light source apparatus according to claim 1,
wherein the light source comprises a light-emitting element that emits light and a wavelength sweep unit that sweeps the wavelength of the light emitted from the light emitting element according to the predetermined cycle, and
the control unit controls wavelength sweep characteristics in the wavelength sweep unit as the control parameter of the light source, thereby to set a timing of the mode hop detected by the mode hop detector outside of the specified period.

5. The wavelength-swept light source apparatus according to claim 1, wherein the control unit controls a relative position of the specified period to the predetermined cycle as a parameter that defines the specified period, thereby to set a timing of the mode hop detected by the mode hop detector outside of the specified period.

6. The wavelength-swept light source apparatus according to claim 1, wherein the mode hop detector is a light intensity sensor that detects a light intensity of the wavelength-swept light emitted from the light source, and performs detection of the mode hop based on a change of the detected light intensity.

7. The wavelength-swept light source apparatus according to claim 1, wherein the mode hop detector is a frequency detector that detects a frequency of the wavelength-swept light emitted from the light source, and performs the detection of the mode hop based on a relation between the detected frequency and a light intensity corresponding to the frequency.

8. The wavelength-swept light source apparatus according to claim 1, further comprising:
a light splitting element that splits the wavelength-swept light emitted from the light source into two;
a first optical path that passes one of the split wavelength-swept light;
a second optical path that passes the other of the split wavelength-swept light;
a combining element that combines the one of the wavelength-swept light that has passed through the first optical path and the other of the wavelength-swept light that has passed through the second optical path thereby to generate an interference light; and
a light receiving element that detects an interference signal based on the interference light,
wherein the mode hop detector detects the mode hop based on a time change of a signal strength in the interference signal.

9. A measuring apparatus comprising:
the wavelength-swept light source apparatus according to claim 8; and
an analysis unit that acquires the interference signal in the specified period and obtains a position of each part of the object to be measured based on a peak in a relation between a frequency of the acquired interference signal and a signal strength corresponding to the frequency,
wherein the second optical path passes the other of the split wavelength-swept light toward to the object to be measured as well as the other of the wavelength-swept light reflected from the object to be measured, and
the combining element combines the one of the wavelength-swept light that has passed through the first optical path and the other of the wavelength-swept light that has been reflected from the object to be measured and has passed through the second optical path thereby to generate an interference light.

10. The wavelength-swept light source apparatus according to claim 1, further comprising:
a light splitting element that splits the wavelength-swept light emitted from the light source into two;
a first optical path that passes one of the split wavelength-swept light;
a second optical path that passes the other of the split wavelength-swept light;
a combining element that combines the one of the wavelength-swept light that has passed through the first optical path and the other of the wavelength-swept light that has passed through the second optical path thereby to generate an interference light; and
a light receiving element that detects an interference signal based on the interference light,
wherein the mode hop detector detects the mode hop based on a shape of a peak in a relation between a frequency of the interference signal and a signal strength corresponding to the frequency.

11. A measuring apparatus comprising:
the wavelength-swept light source apparatus according to claim 1;
a light splitting element that splits the wavelength-swept light emitted from the wavelength-swept light source apparatus into two;
a first optical path that passes one of the split wavelength-swept light;
a second optical path that passes the other of the split wavelength-swept light towards an object to be measured and the other of the wavelength-swept light reflected from the object to be measured,
a combining element that combines the one of the wavelength-swept light that has passed through the first optical path and the other of the wavelength-swept light that has been reflected from the object to be measured and has passed through the second optical path thereby to generate an interference light;
a light receiving element that detects an interference signal based on the interference light; and
an analysis unit that acquires the interference signal in the specified period and obtains a position of each part of the object to be measured based on a peak in a relation between a frequency of the acquired interference signal and a signal strength corresponding to the frequency.

* * * * *